(12) United States Patent
Kanomi et al.

(10) Patent No.: US 8,297,970 B2
(45) Date of Patent: Oct. 30, 2012

(54) ORTHODONTIC BRACKET

(75) Inventors: Ryuzo Kanomi, Hyogo (JP);
Toshimitsu Ohki, Tochigi (JP)

(73) Assignee: Dentsply-Sankin K. K., Ohtawara-shi (JP)

( * ) Notice: Subject to any disclaimer, the term of this patent is extended or adjusted under 35 U.S.C. 154(b) by 0 days.

(21) Appl. No.: 12/922,967

(22) PCT Filed: Mar. 18, 2009

(86) PCT No.: PCT/JP2009/055253
§ 371 (c)(1),
(2), (4) Date: Sep. 16, 2010

(87) PCT Pub. No.: WO2009/116560
PCT Pub. Date: Sep. 24, 2009

(65) Prior Publication Data
US 2011/0020762 A1    Jan. 27, 2011

(30) Foreign Application Priority Data
Mar. 18, 2008 (JP) .................................. 2008-069897

(51) Int. Cl.
*A61C 7/14* (2006.01)
(52) U.S. Cl. ........................................... 433/13; 433/11
(58) Field of Classification Search ................ 433/7–12, 433/13, 14, 16; D24/180
See application file for complete search history.

(56) References Cited

U.S. PATENT DOCUMENTS

| 5,275,557 | A | 1/1994 | Damon | |
|---|---|---|---|---|
| 6,042,373 | A * | 3/2000 | Hermann | 433/13 |
| 6,361,314 | B1 * | 3/2002 | Garton, Jr. | 433/8 |
| 6,843,651 | B2 | 1/2005 | Orikasa | |
| 2007/0248928 | A1 * | 10/2007 | Damon | 433/10 |

OTHER PUBLICATIONS

International Search Report of PCT/JP2009/055253, mailing date Apr. 28, 2009.

* cited by examiner

*Primary Examiner* — Cris L Rodriguez
*Assistant Examiner* — Matthew Seward
(74) *Attorney, Agent, or Firm* — Westerman, Hattori, Daniels & Adrian, LLP

(57) ABSTRACT

The orthodontic bracket according to the present invention is provided with ligating means having a simple configuration, has additional functions for improving therapeutic effect and improving aesthetic appearance and enables maintenance to be carried out easily. A movable slider portion 2 for pinching an upper portion and a lower portion of an archwire to hold the archwire is provided in order to hold the archwire with respect to a bracket body 1 that has a slot 5 for holding the archwire. This slider portion 2 is inserted into the bracket body 1 to thereby hold the archwire 6. An orthodontic bracket composed of the bracket body 1 and the slider portion 2 has aesthetic properties by having a rounded shape with few surface irregularities. The slider portion 2 can be readily moved with an operating tool 14 and can be easily attached and detached.

10 Claims, 25 Drawing Sheets

ORTHODONTIC BRACKET

TECHNICAL FIELD

The present invention relates to an orthodontic bracket used for orthodontic treatment. More particularly, the present invention relates to an orthodontic bracket that improves aesthetic appearance, facilitates ligation of an archwire and has an additional function of improving therapeutic effect.

BACKGROUND OF THE INVENTION

The use of brackets is widely known as orthodontic treatment for malocclusion. Dental arch is corrected by attaching brackets and the like to teeth and applying physical tension, namely a restoring force, such as a pushing force, a pulling-back force or a torsion force, of an archwire attached to these brackets, to the teeth to gradually change the positions of the teeth.

For normal use, a groove is formed in the bracket for causing an archwire to slide or be fixed in the center of the bracket body and the archwire is held in the groove by various ligating means. In the case of emphasizing aesthetic appearance in particular, plastics or ceramics have recently come to be used as materials of such brackets in addition to conventional metal. On the other hand, titanium alloy, stainless steel or other non-rusting materials are used for the material of archwire.

Various modifications of such orthodontic brackets are known. However, though these brackets are made of plastic, they have a groove (slot) and the archwire is held in a constrained state in the groove. Examples of ligating means for archwire include that which holds the archwire by means of wings provided on the outside of the brackets and that of the same configuration which composes a locking member holding the archwire by way of elastic deformation. Moreover, another known example of ligating means is that which employs a configuration holding the archwire by pressing the ligating means onto the brackets from above.

As seen from detailed description of the prior art, an orthodontic bracket is disclosed which is composed so as to hook and hold the archwire with a bent, L-shaped locking member that is made of an elastic plate and has one portion rotatably engaged by a tab formed on the lower portion of a wing as well as has a hooking portion formed at its upper end. (see, for example, Japanese Patent Application Laid-open No. 2007-202: Patent Document 1).

In addition, a bracket is also disclosed that employs a configuration in which guide grooves are provided in wings, the outer walls of the wings are formed roughly in X-shape and, after inserting the archwire into the guide grooves, the archwire is caused to fit into and attached to the X-shaped grooves with a ligature wire or rubber band (see, for example, Japanese Utility Model Laid-open Publication No. H5-63517: Patent Document 2). Moreover, a bracket is disclosed in which a wire is removably ligated by elastically deforming synthetic resin ligating member and causing it to fit into a wire insertion groove formed on a bracket from above (see, for example, Japanese Patent Application Laid-open No. 2004-329912: Patent Document 3). Although the hooking portions are wings in this method as well, this configuration allows the wire to be attached from above the bracket in a single operation.

As was previously described, treatment for correcting dental arch by using an archwire involves repositioning of the teeth while applying force thereto. The archwire is held by brackets with wings using ligating members such as ligature wires or rubber bands. Conventional methods involved pressing the archwire onto the bracket with a pressing force exceeding necessary extent.

In addition, the pushing force on the archwire can be reduced in order to reduce the strength of force applied to teeth. In the case of a conventional ligating method using a ligature wire with wings or a ligating method that uses rubber bands through elastic deformation, pressing force exceeding necessary extent is inevitably applied and attachment and removal of the archwire requires a complex procedure. In addition, conventional ligating members have a complex, involute configuration in which there are numerous irregularities in relation to the bracket.

Consequently, the structure of conventional brackets makes food particle, plaque and other foreign substances apt to remain on them, which is unsanitary. In addition, these brackets also lacked aesthetic qualities. There are many examples of orthodontic treatment using these brackets that employ means for ligating the archwire through wings on the bracket. However, a method in which a ligating member fits into wings from above the bracket to ligate the archwire in a groove in the bracket is a type of self-ligating method and the pressing force by the wire decreases due to the formation of gaps between the ligating member and wire.

Although this method facilitates the initial attachment procedure, the archwire must be repeatedly re-ligated during the course of orthodontic treatment and there is also a problem of the procedure requiring considerable complexity for the orthodontist in operation of attaching and detaching of the archwire. In addition, this composition requires the ligating member to be detached during removal and, due to the extremely small size of the ligating member, there is a risk for the ligating member to fall off. Moreover, since the wings have a protruding portion and the like, there is a problem where aesthetic characteristics are impaired from a Viewpoint of aesthetic appearance.

Another known example of self-ligating is of a type in which a bracket and a ligating member are integrally composed. Namely, a type is known in which an archwire is held by covering the open side of a slot with a shutter (see, for example, Japanese Patent Application Laid-open No. 2005-58742: Patent Document 4 and Japanese Patent Application Laid-open No. 2006-192272: Patent Document 5). In addition, a type is also known in which an archwire is held by covering it with a rotating locking member (see, for example, Japanese Patent Application Laid-open No. 2001-104340: Patent Document 6). Moreover, a type is also known in which an archwire is held by inserting it into a latch (see, for example, Japanese Translation of PCT Application No. 2003-510128 (WO 01/022901): Patent Document 7 and Japanese Translation of PCT Application No. 2006-505327 (WO 2004/041109): Patent Document 8). Although these integrated configurations facilitate the ligation and release procedures, they are all of the self-ligating types, hence they have irregularities with respect to their structure, thereby resulting in the shortcomings of inferior aesthetic properties and cleanability.

In these types of brackets in the prior art, the configurations thereof are not satisfactory in terms of providing orthodontic treatment. Thus, there is a need for a bracket that overcomes the problems of these conventional configurations, reduces the degree of irritation of mucous membranes for the patient, exhibits superior sanitary properties and facilitates the ligation procedure for the orthodontist. In addition, there is also a need for a bracket with which such a superior orthodontic technique is effectuated that facilitates wire control while also enabling a ligation technique with improved aesthetic appearance to be exhibited.

SUMMARY OF THE INVENTION

The present invention has been conceived under the background art as described above and achieves the following objects.

An object of the present invention is to provide an orthodontic bracket that employs a simple composition with slidable ligating means, is able to ligate an archwire by clamping, allows the archwire to be easily replaced with a different archwire, stably and reliably maintains dental arch and allows maintenance to be performed easily.

Another object of the present invention is to provide an orthodontic bracket that employs a simple composition with sliding ligating means, wherein a ligature wire or rubber band can be used in the case of requiring emergency evasive treatment in terms of treatment.

Still another object of the present invention is to provide an orthodontic bracket that has a curved surface with few irregularities and improved aesthetic appearance.

Yet another object of the present invention is to provide an orthodontic bracket having an outer surface in a smooth shape of a curved surface; thereby having satisfactory cleanability due to little adhesion of food residue and the like, being sanitary and facilitating the procedure for wire control.

The present invention is composed of the following means in order to achieve the above-mentioned objects. Namely, the orthodontic bracket according to a first aspect of the present invention is:

an orthodontic bracket for orthodontic treatment, which has a face for joining to a tooth surface in the lower portion thereof and has a groove provided in the center of the body therof and in which an archwire is held so as to slide freely and/or be fixed, the bracket comprising: a bracket body that has a groove for holding the archwire; and a slider portion that is guided by the bracket body and holds the archwire so as to pinch it at upper portion and lower portion thereof in the groove while being able to move relative the bracket body.

The orthodontic bracket according to a second aspect of the present invention is one according to the first aspect of the invention, wherein:

the slider portion has a surface area that is roughly half of that of the bracket body when viewed from above and is configured so as to be able be attached to and detached from the bracket body while moving forward and backward relative to the bracket body along a straight line by means of a guide portion provided on the bracket body and positioned at the lower portion of the archwire.

The orthodontic bracket according to a third aspect of the present invention is one according to the first aspect of the invention, wherein:

the slider portion has a groove for detachment for attaching and detaching the archwire through enabling the slider portion to move for detachment with respect to the bracket body.

The orthodontic bracket according to a fourth aspect of the present invention is one according to the first aspect of the present invention, wherein:

the slider portion has elastically deformable holding portions for fixing and holding the archwire using the elasticity of the slider portion itself at the position of the lower portion of a slot of the bracket body.

The orthodontic bracket according to a fifth aspect of the present invention is one according to the first aspect of the present invention, wherein:

the bracket body and the slider portion are respectively provided, in an outer sidewall thereof, with through grooves in the shape of overhangs that extend along the direction of installation of the archwire.

The orthodontic bracket according to a sixth aspect of the present invention is one according to the first aspect of the present invention, wherein:

the bracket body and the slider portion are provided, in the lower portion of a groove for locking the archwire, with a through groove which extends over both of the bracket body and the slider portion in a direction that transverses the groove for locking the archwire.

The orthodontic bracket according to a seventh aspect of the present invention is one according to the first aspect of the present invention, wherein:

the bracket body and the slider portion are provided, in the surface of the upper portion of a groove for locking the archwire, with a through groove which extends over both of the bracket body and the slider portion in a direction that transverses the groove for locking the archwire.

The orthodontic bracket according to an eighth aspect of the present invention is one according to the first aspect of the present invention, wherein:

the bracket body and the slider portion are provided with recesses and projections mutually engageable and disengageable at contact sites on the upper portion on the archwire locking sidewall.

The orthodontic bracket according to a ninth aspect of the present invention is one according to the third aspect of the present invention, wherein:

the groove for detachment is provided so as to have a cut-out portion, of which one side is open and which has a rectangular cross-section, at the upper position of the archwire to be attached and detached.

The orthodontic bracket according to a tenth aspect of the present invention is one according to the sixth or seventh aspect of the present invention, wherein:

the slider portion is provided with a protruding thick portion at the lower portion of the through groove and the bracket body is provided with a recess into which the thick portion is inserted.

The orthodontic bracket according to an eleventh aspect of the present invention is one according to the ninth aspect of the present invention, wherein:

the groove for detachment has a shape in which one end at the position of the upper portion is open in the lengthwise direction of the archwire.

The orthodontic bracket according to a twelfth aspect of the present invention is one according to the ninth aspect of the present invention, wherein:

the groove for detachment is a groove having a shape into which is inserted an operating tool having an inserting portion that is pushed by the elastic force of an elastic body.

Since the orthodontic bracket according to the present invention is provided with a slider portion that is able to hold an archwire at an upper portion and a lower portion thereof, stable and reliable holding of the archwire can be maintained while also being sanitary due to less likelihood of residual food particles and other residue. In addition, while existing brackets integrating a self-ligating member include those in which the ligating portion is of a shutter type, of a type with a rotating cover that utilizes elasticity or of a mounting type in which the ligating member has been separated, a self-ligating structure is required for the design and has irregularities formed in the surface. In comparison therewith, the orthodontic bracket according to the present invention employs a composition with which self-ligation is carried out by causing guide portions on the outside of a bracket body to slide and moving the entire slider portion which accounts for roughly half in external appearance.

As a result of employing this structure, there are few irregularities in the external shape, including the sliding mechanism portion, allowing a sense of integration to be obtained and the entire bracket is composed of a smooth curved surface free of level differences. As a result, an orthodontic bracket can be obtained that has improved aesthetic appearance. In addition, as a result of adopting a sliding type of ligating means, the procedures for attaching and detaching can be carried out easily with the ligating means still held on the bracket. Moreover, such a composition of a bracket is attained that allows the slider portion to be pulled out and removed as necessary and allows the slider portion to be replaced with a different slider portion by inserting it therein. In other words, the use of such a composition makes it possible to enhance work efficiency of orthodontic treatment while also facilitating maintenance of the orthodontic bracket.

In the orthodontic bracket according to the present invention, the elastic force applied to the teeth by the archwire in cases of prominent crowding of teeth can be reduced, as a result of making contrivances in the portion of a slider through hole or in the manner in which the slider portion itself is used, while conversely, elastic action can be increased by adjusting the gap between the slot and arch wire. Moreover, since the materials of the bracket body and slider portion can be set according to their respective purpose of use, strength can be secured while simultaneously preventing wear of opposing teeth. In addition, the orthodontic bracket according to the present invention also gives advantages in clinical effectiveness in terms of aesthetic appearance, rapid progression of treatment, ease of manipulation and reduced risk and pain for the patient.

DETAILED DESCRIPTION OF PREFERRED EMBODIMENTS

In the following, embodiments of the present invention will be explained with reference to the drawings. In particular, the present invention relates to an orthodontic bracket that has improved ligating means, is configured to facilitate treatment, has a smooth surface and improves aesthetic appearance.

First Embodiment

Figure 1:
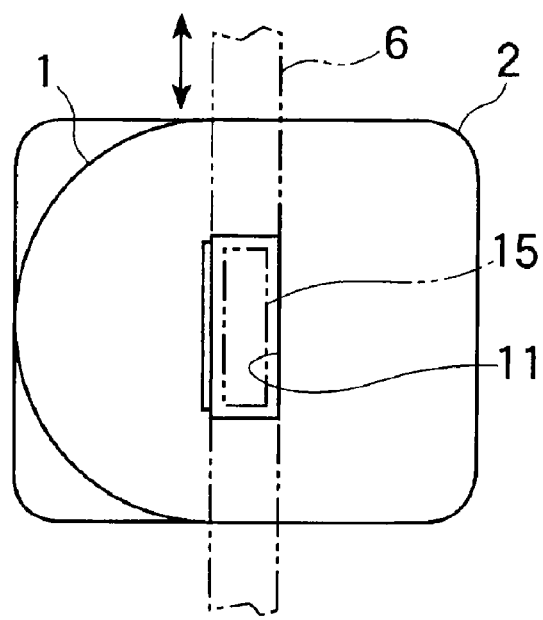
FIG. 1 is a plan view of an orthodontic bracket according to a first embodiment of the present invention.
Figure 2:
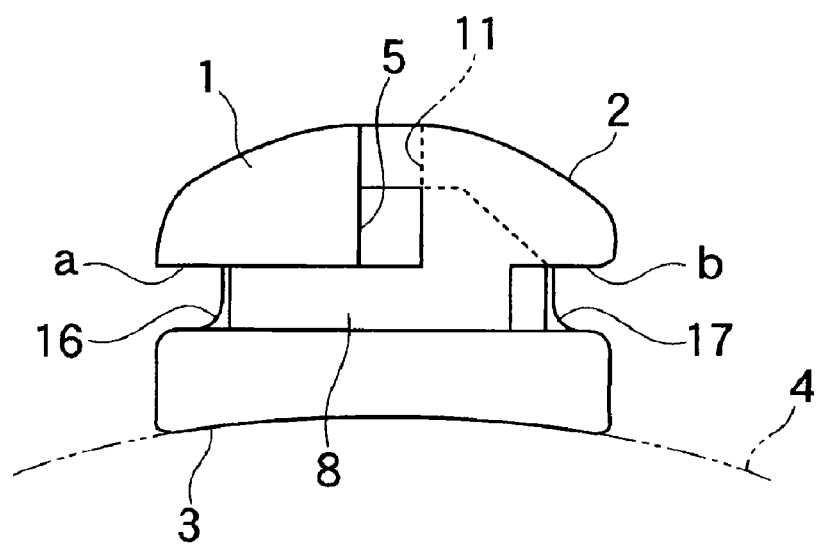
FIG. 2 is a front view of the orthodontic bracket shown in FIG. 1.
Figure 3:
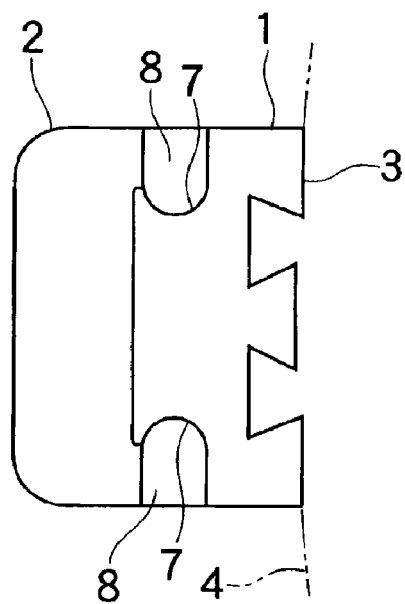
FIG. 3 is a side view of the orthodontic bracket shown in FIG. 1.
Figure 4:
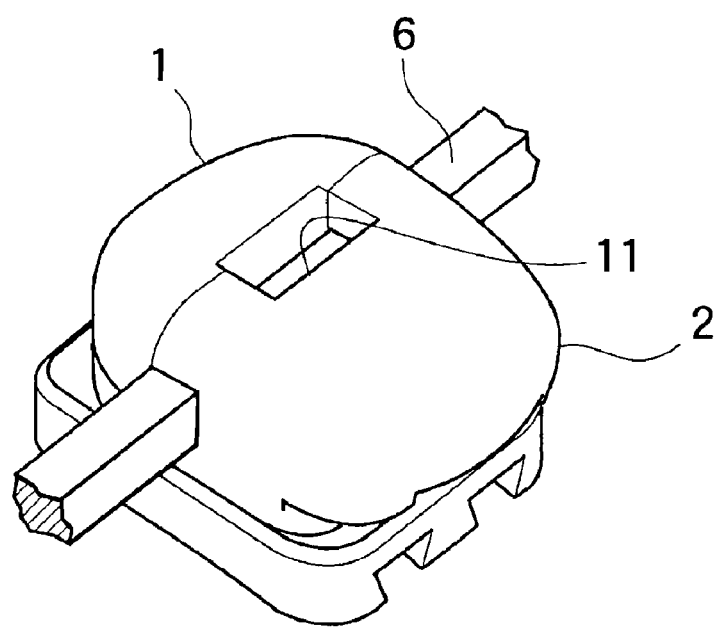
FIG. 4 is an external view of the orthodontic bracket according to the first embodiment.
Figure 5:
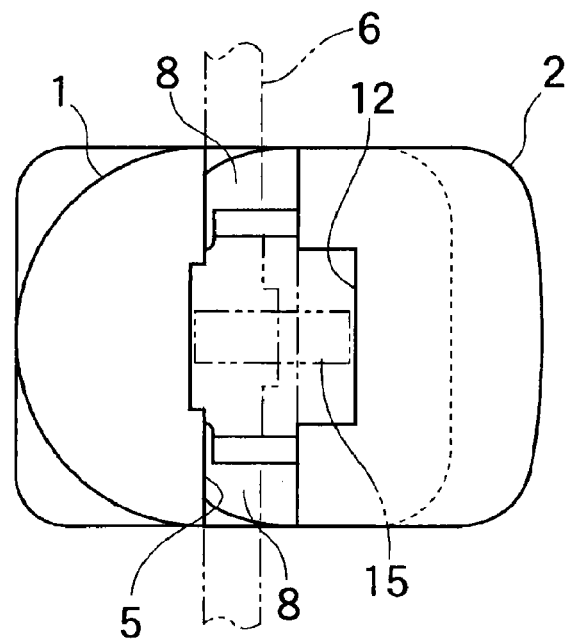
FIG. 5 is a plan view of the orthodontic bracket showing the state in which a slider portion in the first embodiment is extracted.
Figure 6:
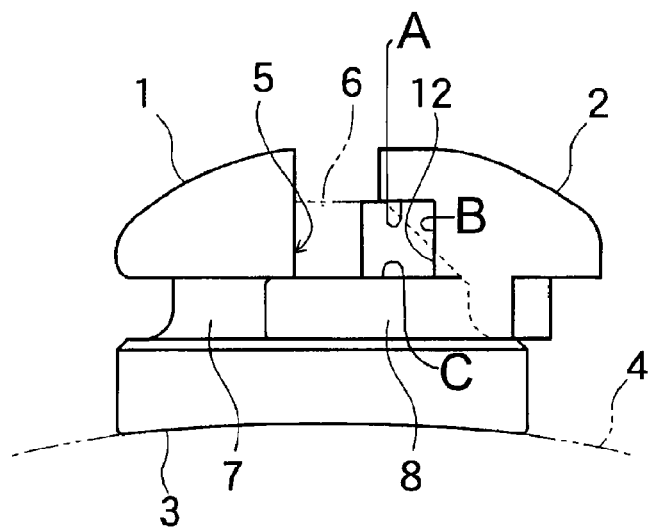
FIG. 6 is a front view of FIG. 5.

FIG. 1 is a plan view of an orthodontic bracket according to a first embodiment of the present invention. FIG. 2 is a front view of the orthodontic bracket shown FIG. 1. FIG. 3 is a side view of the orthodontic bracket shown FIG. 1. FIG. 4 is an external view of the orthodontic bracket according to the first embodiment. FIG. 5 is a plan view of an orthodontic bracket showing a state in which a slider portion in the first embodiment is extracted. FIG. 6 is a front view of FIG. 5.

Figure 7:
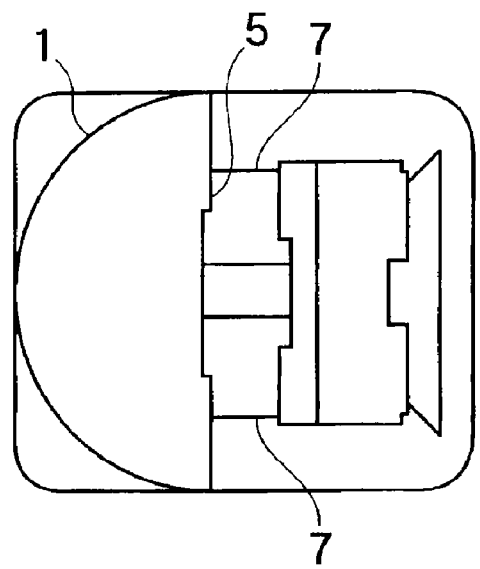
FIG. 7 is a plan view of the bracket body according to the first embodiment.
Figure 8:
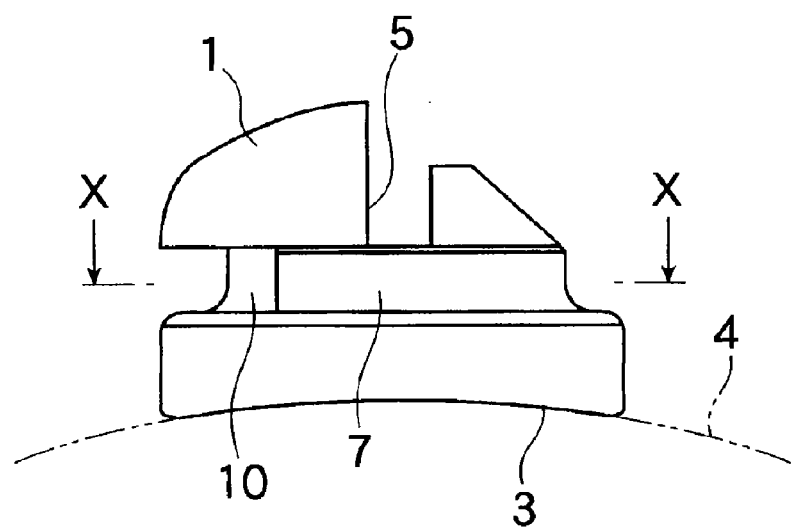
FIG. 8 is a front view of FIG. 7.
Figure 9:
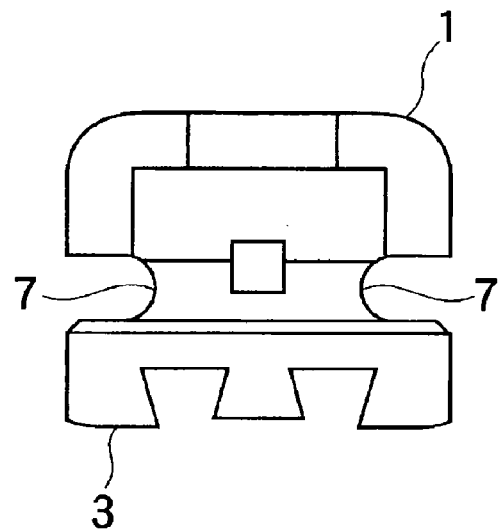
FIG. 9 is a side view of FIG. 7.
Figure 10:
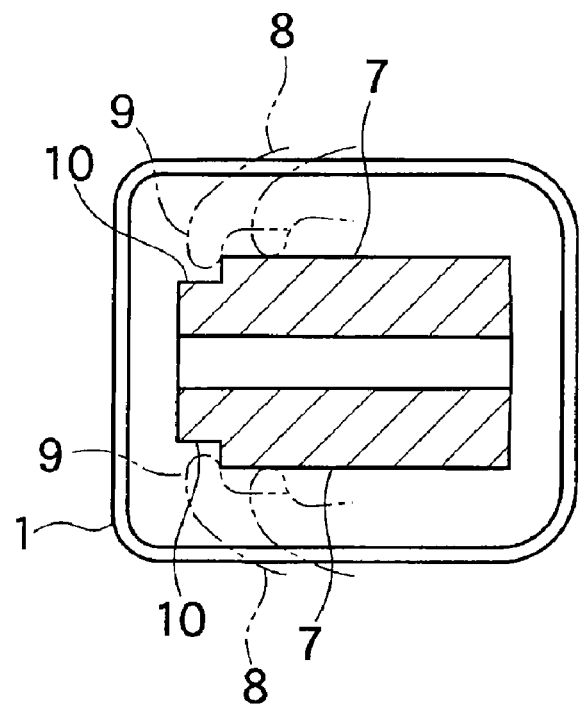
FIG. 10 is a cross-sectional view of FIG. 8 taken along line X-X.
Figure 11:
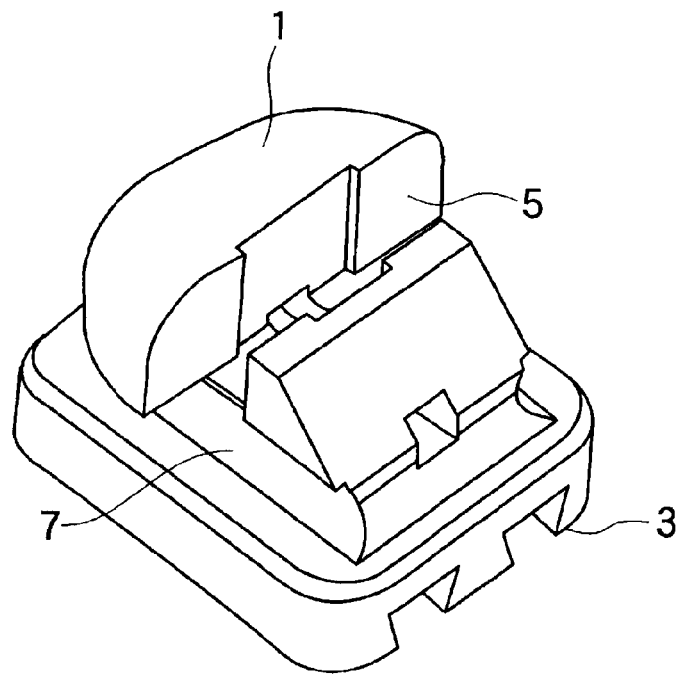
FIG. 11 is an external view showing the bracket body alone in the first embodiment.
Figure 12:
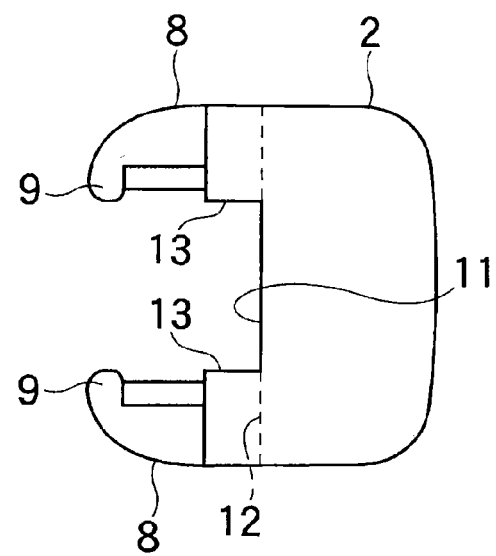
FIG. 12 is a plan view of a slider portion in the first embodiment.
Figure 13:
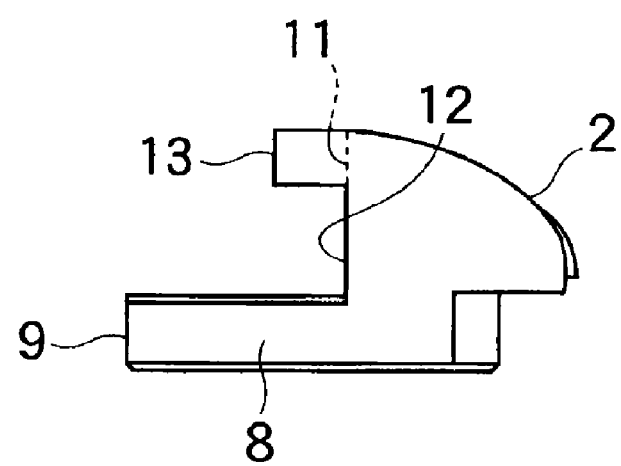
FIG. 13 is a front view of FIG. 12.
Figure 14:
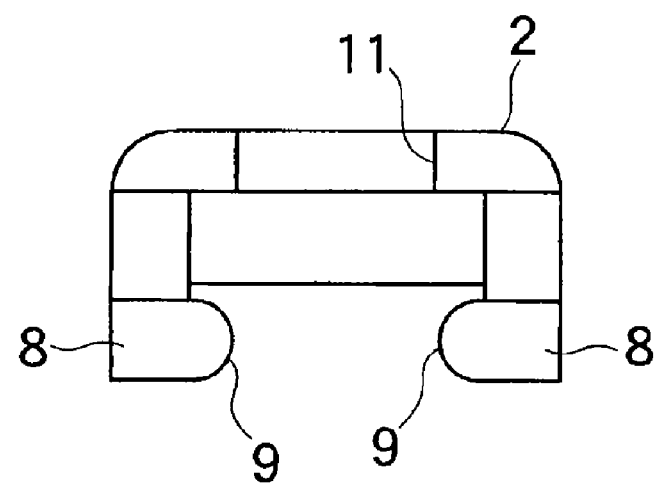
FIG. 14 is a side view of FIG. 12.
Figure 15:
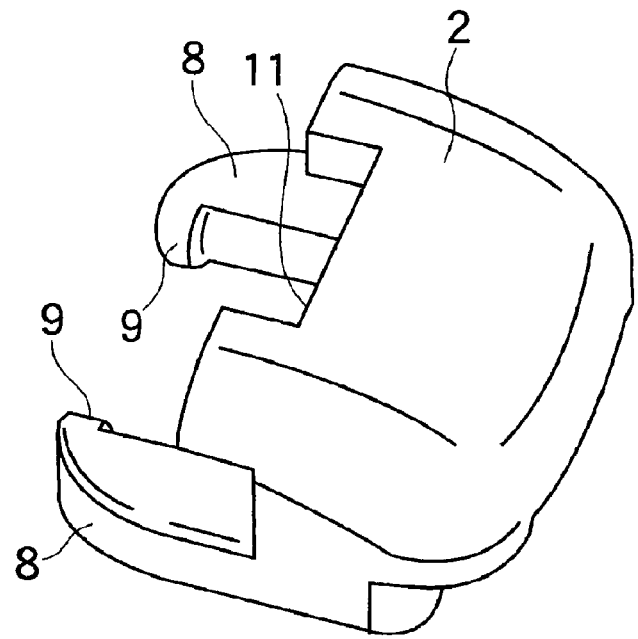
FIG. 15 is an external view showing the slider portion alone in the first embodiment.

FIGS. 7 to 11 are drawings showing the configuration of the orthodontic bracket alone in the first embodiment. FIG. 7 is a plan view of the bracket body in the first embodiment. FIG. 8 is a front view of FIG. 7. FIG. 9 is a side view of FIG. 7. FIG. 10 is a cross-sectional view of FIG. 8 taken along line X-X. FIG. 11 is an external view of the bracket body alone in the first embodiment. FIG. 12 is a plan view of a slider portion in the first embodiment. FIG. 13 is a front view of FIG. 12. FIG. 14 is a side view of FIG. 12. FIG. 15 is an external view of the slider portion alone in the first embodiment.

Figure 16:
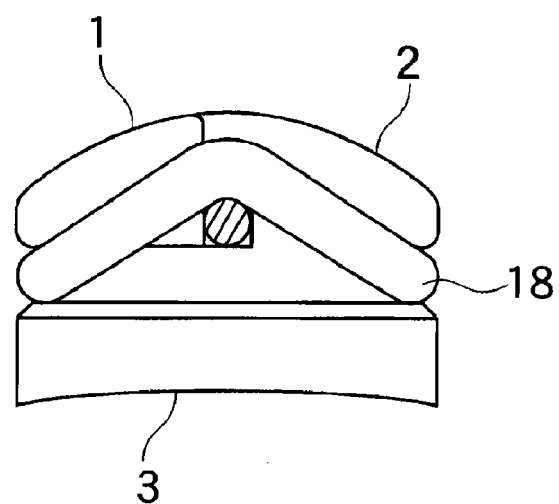
FIG. 16 is a front view of the bracket according to the first embodiment showing an example of archwire held by a rubber band.
Figure 17:
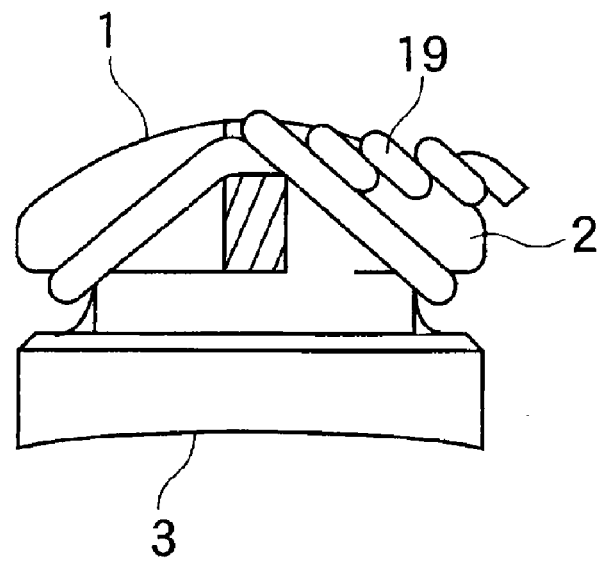
FIG. 17 is a front view of the bracket according to the first embodiment showing an example of archwire held with a ligature wire.
Figure 18:
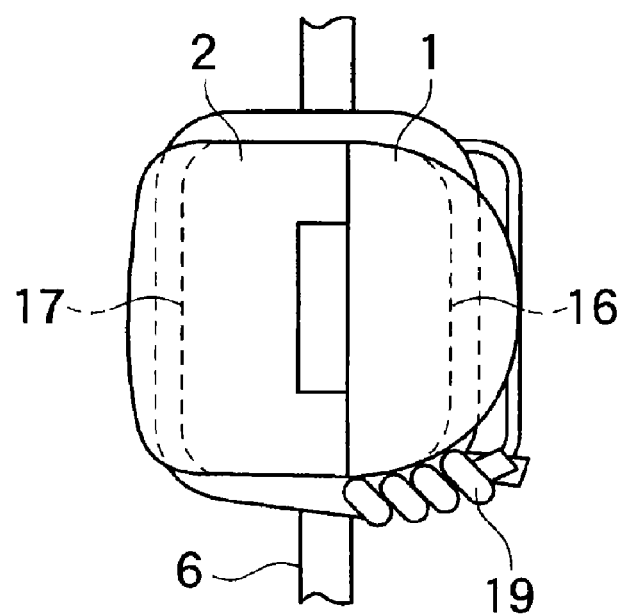
FIG. 18 is a front view of FIG. 17.
Figure 19:
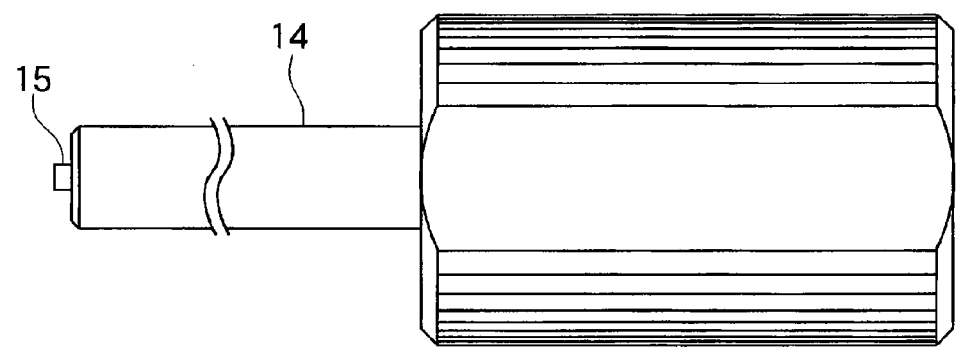
FIG. 19 is a front view of an operating tool.
Figure 20:
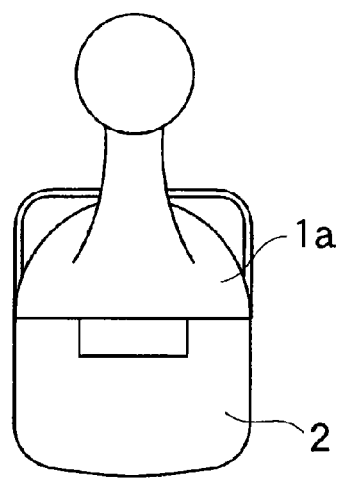
FIG. 20 is a plan view showing the first embodiment in which the orthodontic bracket has been deformed to be an orthodontic bracket provided with a hook.

FIGS. 16 to 18 are drawings showing the first embodiment in which an archwire is held to a bracket body and a slider portion. FIG. 16 is a front view of the orthodontic bracket according to the first embodiment showing an example of an archwire held with a rubber band. FIG. 17 is a front view of the orthodontic bracket according to the first embodiment in which an archwire is held with a ligature wire. FIG. 18 is a plan view of FIG. 17. FIG. 19 is a drawing of an operating tool that operates a slider portion of an orthodontic bracket. FIG. 20 is a plan view showing an orthodontic bracket provided with a hook.

In these drawings, the orthodontic bracket of the present invention is composed of a bracket body 1 and ligating means (referred to as a "slider portion 2" below). This orthodontic bracket is provided with through grooves 16 and 17 for a ligating member such as a rubber band at locations, instead of wings, the through grooves 16 and 17 on both sides are in the shape of overhangs a and b (see FIG. 2) or, in other words, are shaped to have hooking upper portion thereof and the surfaces of the bracket body 1 and the slider portion 2 have a smooth, rounded shape with few irregularities.

The lower surface of the bracket body 1 is in the form of a joining surface 3 that is joined with a tooth and is adhered to a tooth surface 4 by means of an adhesive. In addition, a concave groove, namely a slot 5, is provided in a central portion of the bracket body 1 for holding an archwire 6. The structure of this bracket body 1 is not fixed but rather various types thereof may be made to be available so as to be selected according to the relationship with treatment technique and the like. In addition, the bracket body 1 is available in various types according to the site of the tooth where it is attached, such as a type for an anterior tooth, cuspid, premolar or molar tooth. In addition, since shape also differs due to differences in torque and angulation as well as the orientation of the tooth to be corrected, various bracket bodies may be available in accordance therewith.

As was previously described, the slot 5, having a cross-section in the shape of an upward opening letter "U", is provided in a central portion of the bracket body 1 in order to cause an archwire 6 to fit therein while moving and adjusting in the directions of the arrows. The material of the bracket body 1 is one type selected from a known plastic, ceramics or metal and the like. In addition, it may be composed of a composite material that is a combination thereof. The slider portion 2 for ligating the archwire 6 is able to move backward and forward along a straight line on the bracket body 1 in a state in which the slot 5 intervenes between the sidewalls of the slider portion 2 and of the bracket body 1. Namely, the slider portion 2 is provided so as to move relative to the bracket body 1.

While the orthodontic bracket according to the first embodiment is mainly composed by the bracket body 1 and the slider portion 2 as described above, the slider portion 2 fits into guide portions 7 provided in parallel with the bracket body 1 and movably slides backward and forward in a prescribed direction with respect to the bracket body 1. On the other hand, a pair of arms 8 is provided on the slider portion 2 in a state of protruding outwards and the distal end of each arm 8 composes a sliding portion 9.

In addition, the arms 8 are of an elastically deformable configuration. The sliding portions 9 pinches, with its paired constitution, the guide portions 7 of the bracket body 1, which are guided with constraint in the vertical direction. When the sliding portions 9 are inserted and guided by the guide portions 7, the arms 8 is elastically deformed and are spread outwards (see FIG. 10). In addition, steps 10 are formed at the ends of the guide portions 7 and these steps 10 are recessed lower than the guiding portions of the guide portions 7.

The material of the slider portion 2 may be the same as or different from that of the bracket body 1. Since there are many cases in which the orthodontic brackets contact with opposing teeth, it is necessary to adopt measures for preventing wear of the opposing teeth and inhibiting wear of the orthodontic brackets themselves. Consequently, it is clinically effective to adjust the hardness of the slider portion 2 that is located on the occlusion side for both the upper and lower jaw and is apt to contact with opposing teeth. For example, orthodontic brackets for anterior teeth of the lower jaw frequently contacts with anterior teeth of the upper jaw. Recently, for ceramic brackets, which are frequently used to take advantage of the aesthetic properties of the material, problems have been indicated which involves wear of opposing teeth due to their high hardness.

The slider portion 2 in this embodiment is located on the occlusion side of a tooth and, as shown in FIG. 1, the opposing teeth contact with the slider portion 2 in nearly all cases, since the surface area thereof, when viewed from above, accounts for roughly half of the total surface area. In addition, the volume ratio of the bracket body 1 to the slider portion 2 is roughly 2:1. Namely, the surface area and volume of the slider portion 2 can be understood to be relatively large in comparison to a conventional shutter type. As a result, the slider portion 2 is able to slide with a large stroke thereby improving workability when the archwire 6 is inserted into the slot 5. In addition, it is effective to select a material that does not damage opposing teeth for the material of the slider portion 2 and select a different material for the bracket body 1 that requires high strength. Ability to change the materials of the bracket body 1 and the slider portion 2 in this manner makes it possible to make individual accommodations corresponding to differences in the material properties and physical properties required for each.

When the sliding portions 9 are pushed in by sliding in a direction perpendicular to the lengthwise direction of the slot 5 of the bracket body 1, the sliding portions 9 fit into the steps 10 at their terminal ends, elastic deformation of the arms 8 is released and the sliding portions 9 are locked in position (see FIG. 10). Although the steps 10 are shown to have a flat shape in the drawing, they may also be formed to be shapes of notches that allow the sliding portions 9 to fit therein. When in this state, the slider portion 2 self-ligates the archwire 6 inserted into the slot 5.

As a result, the slider portion 2 cannot be detached from the bracket body 1 unless an external force is forcibly applied that separates the sliding portions 9 from the steps 10. FIG. 1 shows a state in which the archwire 6 is ligated as a result of the slider portion 2 being pushed into the bracket body 1, while FIG. 5 shows the same configuration in a state in which the archwire 6 is released with the slider portion 2 being extracted.

Next, an explanation will be made for a configuration in which the slider portion 2 is extracted from the bracket body 1. A concave slider groove 11 is provided in a central portion of the slider portion 2 on the side of the bracket body 1. This slider groove 11 is a cut-out portion for extracting the slider portion 2 from the bracket body 1. The shape of the slider groove 11 is that of a long groove extending lengthwise in a direction perpendicular to the direction of extraction.

As shown in the drawings, a through groove 12 is provided in the slider portion 2 for enabling the archwire 6 to be inserted and held by pinching. The lower portion of the slider portion 2 is provided with the arms 8 and the sliding portions 9 on both sides of the through groove 12 and the upper portion is provided with flanges 13 for pinching the archwire 6. The slider groove 11 is provided in a central portion between the flanges 13 and the area there above is open. Namely, the slider portion 2 pinches the archwire 6 in the manner of the letter "U" with the flanges 13 of the upper portion excluding the slider groove 11 and the arms 8 of the lower portion. As shown in FIG. 6, the archwire 6 is guided by the through groove 12 of the slider portion 2. Specifically, the archwire 6 is guided by the three surfaces of guide surfaces A, B and C of the through groove 12. In contrast, since in a bracket of conventional shutter type an archwire is guided by, for example, only a surface A on one side. Thus, in the present invention, more stable guiding and attachment are possible in comparison with conventional sliding types.

In addition, apart from the orthodontic bracket, a tool for extracting the slider portion 2 from the bracket body 1, namely a slot opener 14, is prepared (see FIG. 19). The end of the slot opener 14 composes a rectangular projection 15 and the shape of this projection 15 matches the shape of the slider groove 11 so as to be able to be inserted therein. The width of the projection 15 in the lengthwise direction of the rectangle is set so that the slot is opened by the width of the open surface of the slot so as to enable attachment and detachment regardless of the size of the archwire 6.

In the case of extracting the slider portion 2 from the bracket body 1, the projection 15 of the slot opener 14 is first caused to fit into the slider groove 11 (see FIG. 1). This is performed manually by an orthodontist. Next, the slot opener 14 is rotated by 90 degrees (see FIG. 5). The rotation of the slot opener 14 causes the lengthwise portion of the projection 15 to change its direction into that for extraction of the slider portion 2 and the slider portion 2 is forcibly pushed apart by an amount equivalent to the width of the projection 15 in the lengthwise direction of the rectangle and extracted from the bracket body 1.

At this time, while the arms 8 are elastically deformed and the sliding portions 9 ride up onto the guide portions 7 from the steps 10, the slider portion 2 is maintained in a state held on the bracket body 1. When in this state, the archwire 6 is released and can be easily removed. When the slider portion 2 is impelled towards the archwire 6 after an archwire for replacement has been inserted, the sliding portions 9 again fit into the steps 10, enabling a ligated state to be realized again.

If the width of projection 15 in the lengthwise direction of the rectangle of the slot opener 14 and that of the slider groove 11 are set so as to open by the width of the slot open surface, use of the slot opener 14 results in spreading by a fixed width at all times, thereby preventing the slider portion from falling off due to excessive spreading. This method is safer than one using a tool such as a dental probe for extraction by hooking on a shutter or rotating cover on a ligated site, has little impact on teeth and is free of dispersion of ligating members as is observed for a separate type in which ligating members are removed by cutting.

In such a manner, attachment and detachment of the archwire 6 can be carried out easily only by causing the slider portion 2 to slide along a straight line and, since the slider portion 2 is held on the bracket body 1, it is prevented from falling off and there is no risk of the slider portion 2 coming off from the bracket body 1. In addition, in the case of replacing the slider portion 2 with a slider portion of different specifications or in the case where the slider portion 2 has been damaged, the damaged slider portion 2 alone can be extracted with pliers, without having to remove the bracket body 1, and can be replaced with a new slider portion 2 by insertion into the bracket body 1. In such a manner, the orthodontic bracket can be managed stably. Thus, the configuration enables easy maintenance.

In addition, the slider groove 11 also serves as a marker when the orthodontic bracket is installed on teeth. While the bracket body 1 is fixed in position through adhesion in a state in which it is completely impelled onto the bracket body 1 (see FIG. 1), the rectangular groove of the slider groove 11 serves as a marker for the center and for horizontal direction of the slot 5 of the bracket body 1 and is effective for visually positioning in the case of attaching the bracket body 1 to a tooth. In addition, this rectangular groove can also be used as a guide for attaching the bracket body 1 to a positioning tool in the case of using the tool.

While an orthodontic bracket is basically provided with a slot for inserting an archwire in a central portion thereof and wings in their sidewalls in the majority of cases, through grooves 16 and 17 are respectively provided in the outer sidewall of the bracket body 1 and the outer sidewall of the slider portion 2 parallel to the direction in which the archwire is installed in the present invention (see FIG. 2). Namely, an overhang a is provided for the through groove 16 in the outer sidewall of the bracket body 1 and an overhang b is provided for the through groove 17 in the outer sidewall of the slider portion 2.

Ligation can be performed by hooking a rubber band 18 on the overhangs a and b of the through grooves 16 and 17 respectively as shown in FIG. 16 or by hooking a ligature wire 19 similarly on the overhangs a and b as shown in FIGS. 17 and 18 as necessary. The example shown in FIG. 16 can be applied in the initial stage of orthodontic treatment in cases of using a thin archwire. Namely, the archwire during the course of orthodontic treatment is impelled towards the bottom of the slot 5 through ligating with the rubber band 18.

While force acts towards the center on the overhangs a and b in ligated state, the slot is deformed to the inside in the case of inadequate strength of the orthodontic bracket, since ligation is strong in the case of fixing an archwire with a ligature wire 19. However, a significant characteristic of this embodiment is that the archwire is pinched by mutual U-shaped grooves of the bracket body 1 and the slider portion 2, hence the archwire is held through being surrounded by a rectangular box. The resulting structure is resistant to deformation in the final stage of orthodontic treatment as shown in FIGS. 17 and 18.

Depending on the treatment contents, there are cases in which an orthodontic bracket provided with a hook may be used as shown in FIG. 20. In this case, although a bracket body 1a is provided with a hook, the slider portion 2 has the same configuration as previously described with the slider groove 11 in a central portion thereof, thus allowing it to be used commonly in either case. The lower surface of the bracket body 1a is the face 3 for joining that is joined to a tooth as previously described and is adhered to the tooth surface 4 by means of adhesive. The basic structure and function of these bracket bodies with respect to teeth are known to public, so a detailed explanation thereof is omitted. While the above description has provided explanation of an embodiment of the basic configuration, the following will provide explanation of other embodiments in relation to the holding method.

Second Embodiment

Figure 21:
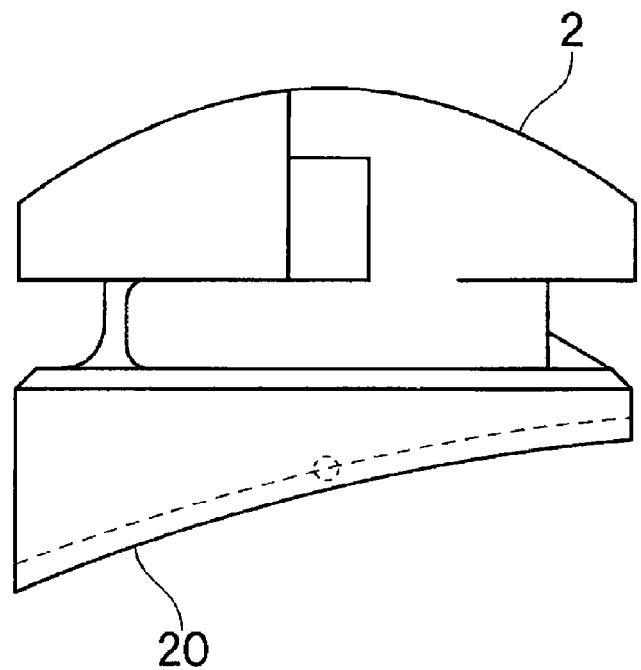
FIG. 21 is a front view showing an orthodontic bracket according to a second embodiment of the present invention that is aligned with anterior maxillary teeth.

Explanation of a second embodiment will be made in accordance with FIGS. 21 and 22. FIG. 21 is a front view showing a second embodiment, which exemplifies an orthodontic bracket that is aligned with an anterior maxillary tooth. Although the shape of the face 20 for joining to a tooth and its surroundings in this embodiment differs from one in the embodiment mentioned above and the shape of the bracket body also differs, the configuration of the slider portion 2 is completely identical. While the configuration is not shown, it is the same for other teeth as well.

Figure 22:
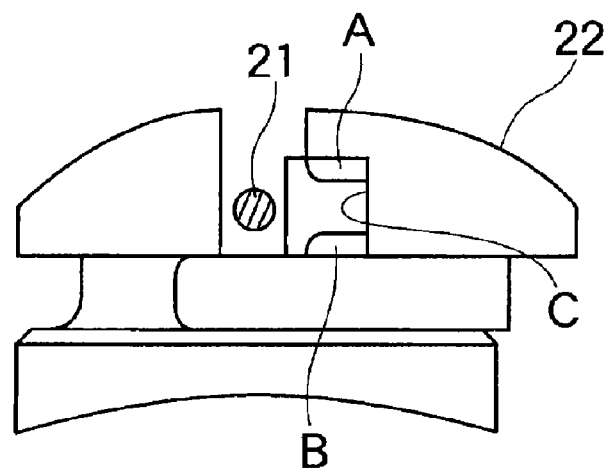
FIG. 22 is a front view showing another example of an orthodontic bracket compatible with a thin archwire in the second embodiment.

FIG. 22 shows an example in which elastic action of a wire is increased in the case of a thin archwire 21. While the above-mentioned slider portion 2 is composed to match standard slot dimensions, a gap is formed between the archwire 21 and the through groove 12 of the above-mentioned slider portion 2 in the case where the width dimension of the archwire 21 is small. There are cases in which an intended elastic effect is required depending on symptoms. In order to fully take advantage of the action of the archwire 21, one with a different configuration is prepared in which thickness is added in terms of shape above and below the through groove as indicated by letters A and B in FIG. 22. The aim of this configuration consists in that, while a thin wire is used in order to prevent excessive force from being applied to teeth particularly during leveling in the initial stage of treatment and the gap between the slot and wire becomes large under normal circumstances, a configuration with the gap reduced can be used when the action of the archwire 21 is to be controlled.

In addition, the width dimension of the thickened portions on both sides of the slot indicated with A and B in the drawing may also be smaller than the wire diameter. As a result, since the archwire 21 is held in a state to be pinched by the slot groove by causing the archwire 21 to fit into the slot by means of elasticity of a slider portion 22, frictional resistance can be imparted to the archwire 21. As a result, ligation action similar to one with a ligature wire or rubber band is obtained. In the slider portion 22, the thicknesses of three surfaces indicated by A, B and C in the drawing can also be increased. Thus, control of this archwire can be carried out in units of individual brackets bodies for each tooth.

If different types of sliders 22 having different thicknesses indicated with A and B of the slider portion 22 corresponding to the size of the archwire 21 are respectively prepared, ligation can be immediately accommodated by selecting and exchanging a suitable slider portion corresponding to the object of treatment. Thus, even if the slider portion is replaced accompanying a change in size of the archwire 21, there is no change whatsoever in the overall shape of the orthodontic bracket.

Third Embodiment

Next, an explanation of a third embodiment will be made in accordance with FIGS. 23 to 29. This embodiment is an example of accommodating orthodontic treatment in the case of prominent crowding of teeth; In cases in which an archwire cannot be inserted into the slot in ordinary manners, unnecessary force ends up being excessively applied to the teeth when the archwire is forcibly inserted into the slot. In order to avoid this in such cases, the archwire of a bracket of a known wire ligating type is weakly ligated with a ligature wire with a portion of the archwire inserted into the slot and left in a suspended state. Further, in the case of a known self-ligating type of bracket in which the slot is covered, the cover portion can be left open by suspending a portion of the archwire from the slot. Moreover, since a ligature wire or rubber band cannot be used in the absence of wings, the configuration mentioned below is employed.

Figure 23:
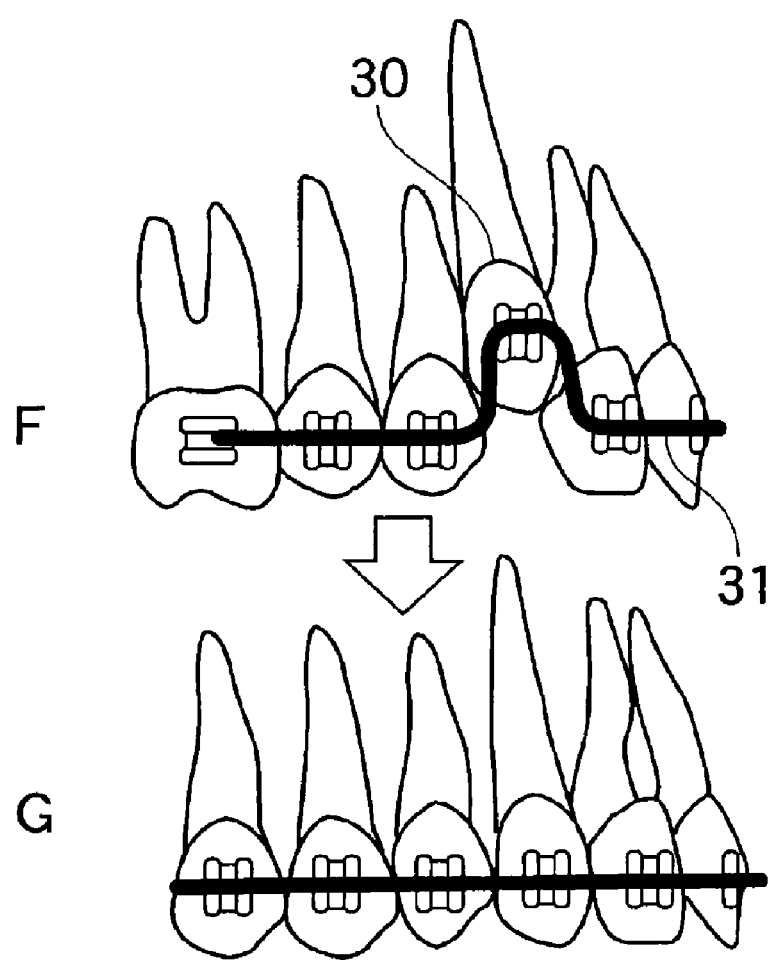
FIG. 23 is an explanatory drawing exemplifying the state in which an archwire is strongly bent towards the gingival side in a third embodiment of the present invention.
Figure 24:
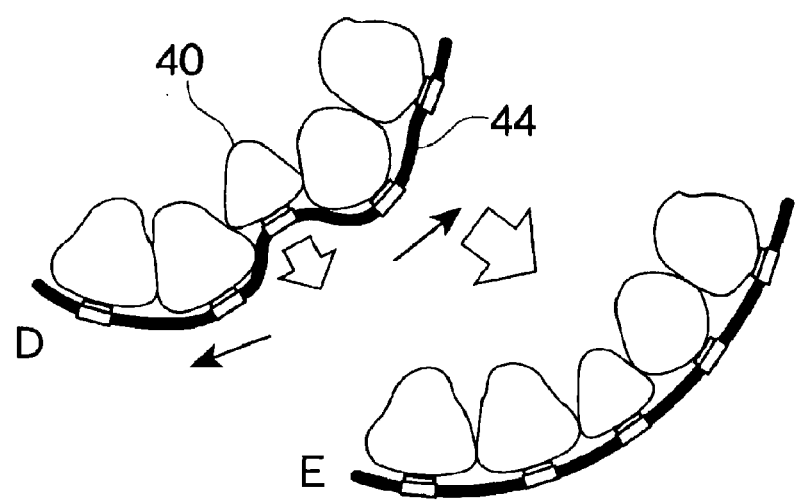
FIG. 24 is an explanatory drawing exemplifying the state in which an archwire is strongly bent towards the lingual side in the third embodiment.

FIGS. 23 and 24 show an embodiment in which an archwire is strongly bent in the direction of the gingival side or lingual side, respectively. FIG. 23 shows an embodiment in which an archwire 31 is strongly bent towards the gingival side and a misaligned tooth 30 is moved towards the occlusion side while pushing apart the teeth on both sides. Ultimately, the teeth are corrected from the state indicated by F in FIG. 23 to the state indicated by G in FIG. 23.

Figure 25:
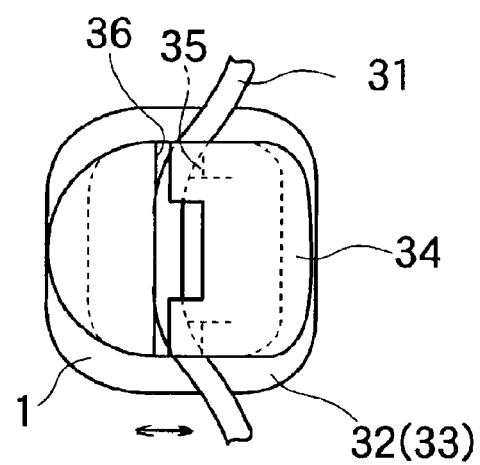
FIG. 25 is a plan view of the orthodontic bracket showing a configuration in which an archwire is held on a bracket body with a slider portion slightly opened in the third embodiment.
Figure 26:
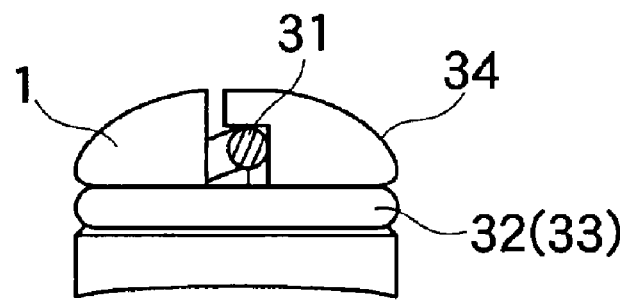
FIG. 26 is a front view of the orthodontic bracket showing a configuration in which a rubber band or ligature wire is held by pressing a slider portion alone onto a bracket body in the third embodiment.
Figure 27:
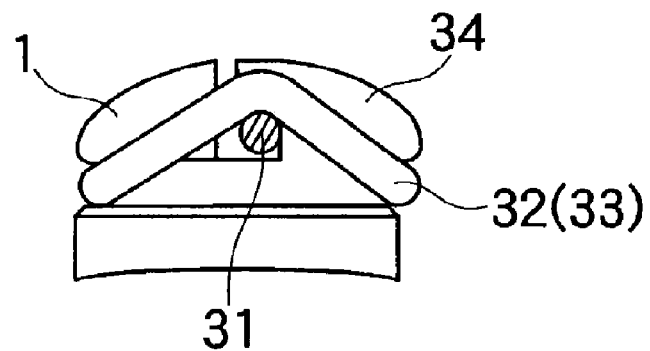
FIG. 27 is a front view of the orthodontic bracket showing a configuration in which a rubber band or ligature wire is held by hooking it on upper portion of an archwire and pressing a slider portion onto the bracket body in the third embodiment.

In this case, a fixing method that uses a rubber band 32 or ligature wire 33 as shown in FIGS. 25 to 27 may be employed to house the strongly bent archwire 31 in the slot and reduce the force applied to the teeth. In this case, since one end of the archwire 31 is constrained by a through groove 35 of a slider portion 34, the slider portion 34 is left open without closing it forcibly. Since both ends of the slot of the bracket body 1 are spread wider than the through groove 35, the archwire 31 is given an allowance in the directions of the arrows (see FIG. 25).

FIG. 26 is a drawing showing a state in which only the slider portion 34 and the bracket body 1 at the lower portion of the slot are held by clamping them without the upper side of the archwire 31 being covered by the rubber band 32 or the ligature wire 33. FIG. 27 is a drawing showing a state in which the bracket body 1 and the slider portion 34 are held by clamping them with the rubber band 32 or ligature wire 33 extending over the upper side of the archwire 31. FIGS. 26 and 27 illustrate methods for locking the slider portion 34 with the rubber band 32 or ligature wire 33 so that it does not open. By fixation in such a manner, the misalignment of teeth 30 is ultimately corrected from the state indicated by F in FIG. 23 to the state indicated by G in FIG. 23.

Figure 28:
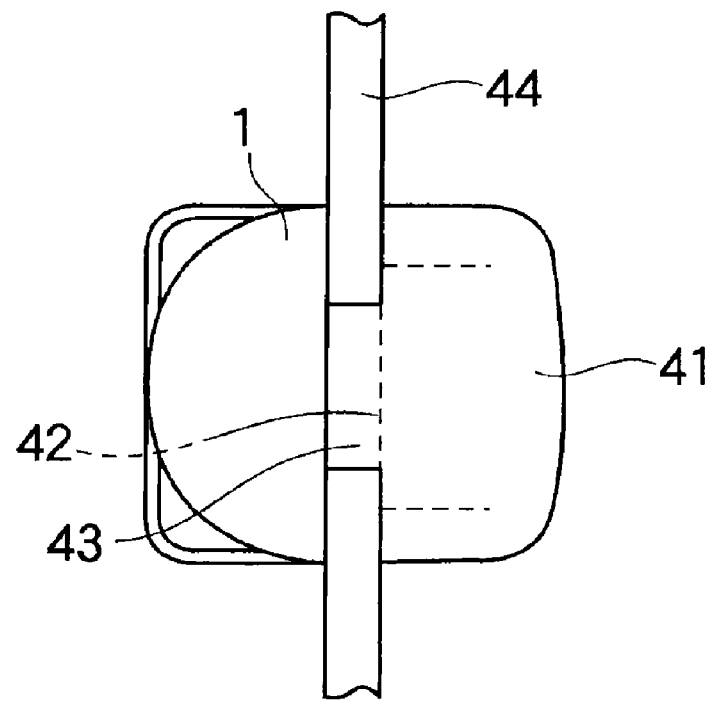
FIG. 28 is a plan view of the orthodontic bracket showing a configuration in which both ends of the upper portion of a through groove are open and an archwire is held in a central portion thereof in the third embodiment.
Figure 29:
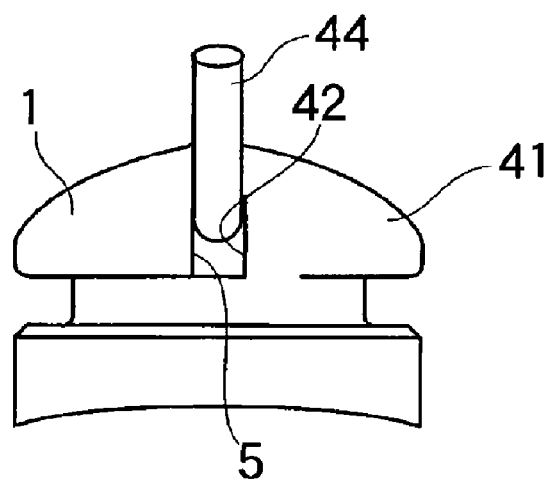
FIG. 29 is a front view of FIG. 28.

FIG. 24 is a drawing showing an embodiment in which an archwire is strongly bent towards the lingual side. This drawing shows a state in which a misaligned tooth 40 is moved towards the labial side while pushing apart the teeth on both sides. Ultimately, the dental arch is corrected from the state indicated by D in FIG. 24 to the state indicated by E in FIG. 24. In this case, a slider portion 41 is prepared having a configuration in which both ends of the upper surface of a through groove 42 of a slider portion 41 are left open and an archwire 44 is held in a central portion 43 of the slider portion 41 as shown in FIGS. 28 and 29.

The slider portion 41 is in a state that prevents, the archwire 44 from detaching outwards as a result of inserting the archwire 44 into the slot 5 of the bracket body 1. Namely, force that acts on the teeth can be reduced together with being able to hold the archwire 44 in the slot 5. In addition, the previously described embodiments may be applied to this embodiment. Namely, in the case where considerable force is applied to not only the labiolingual side but also to the gingival-occlusion side, the slider portion 41 is opened slightly without closing it completely so that corrections are made gradually. During the course of correction in this manner, the slider portion can be replaced with a standard slider portion at the stage where a certain degree of improvement has been achieved.

Fourth Embodiment

Figure 30:
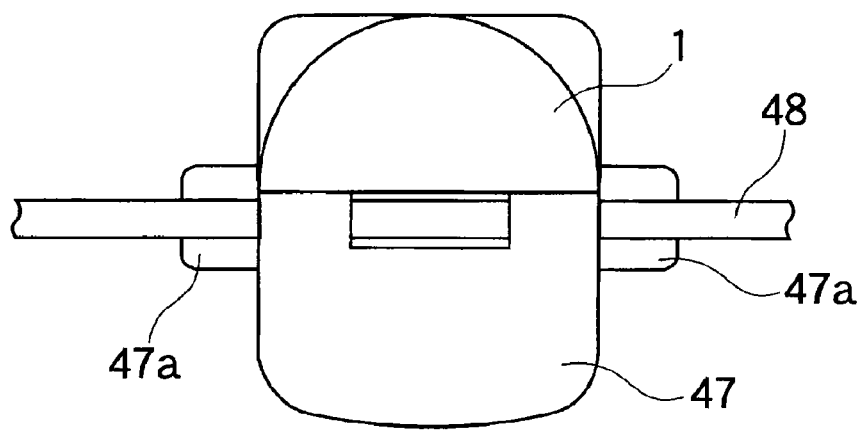
FIG. 30 is a plan view showing an orthodontic bracket according to a fourth embodiment of the present invention having a configuration that provides a guide portion on both sides of a slider portion.
Figure 31:
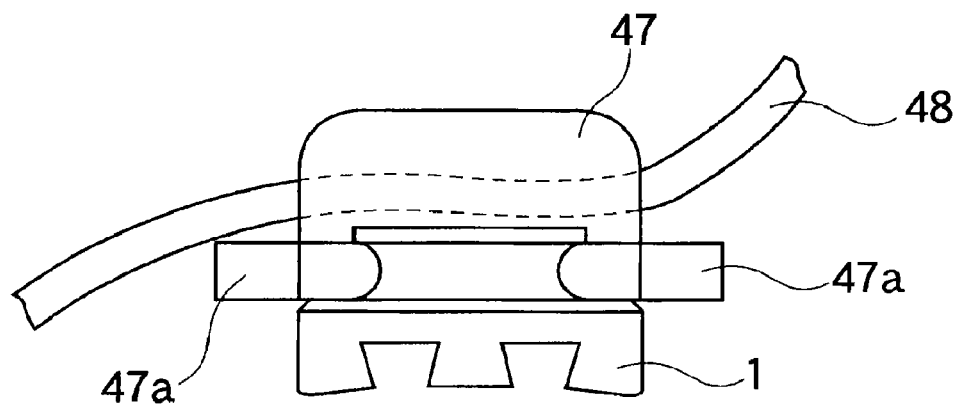
FIG. 31 is a side view of FIG. 30.
Figure 32:
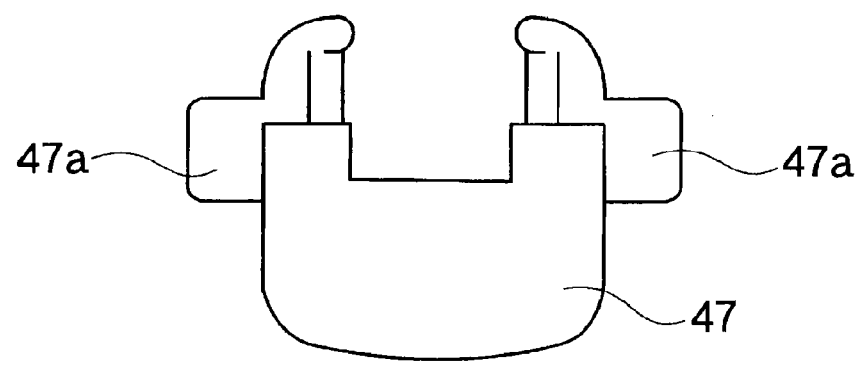
FIG. 32 is a plan view of a slider portion provided with a guide portion on both sides in the fourth embodiment.

Next, explanation of a fourth embodiment will be made in accordance with FIGS. 30 to 32. FIGS. 30 and 31 are drawing showing an orthodontic bracket having a configuration provided with guides on both sides of a slider portion, with FIG. 30 being a plan view and FIG. 31 being a side view. FIG. 32 is a plan view showing the slider portion alone. As shown in FIGS. 30 and 31, this embodiment employs a configuration in which guide portions 47a for guiding an archwire are provided on both sides of a slider portion 47. As shown in FIG. 32, the guide portions 47a are formed on both sides of the slider portion 47 in a direction perpendicular to the protruding direction of the arms. As a result of forming the guide portions 47a on both sides of the slider portion 47 in this manner, action of an archwire 48 can be increased when rotation of a tooth is caused.

Fifth Embodiment

Figure 33:
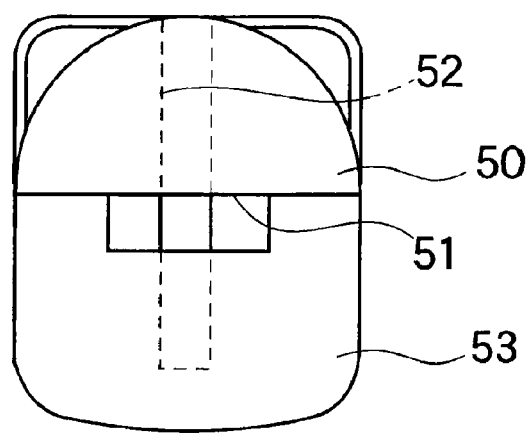
FIG. 33 is a plan view of an orthodontic bracket showing a configuration in which a through hole is provided in a direction perpendicular to a slider portion in a fifth embodiment of the present invention.
Figure 34:
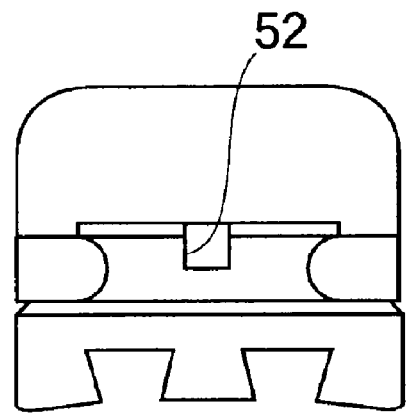
FIG. 34 is a front view of FIG. 33.

In the following, explanation of a fifth embodiment will be made in accordance with FIGS. 33 to 39. FIGS. 33 and 34 are drawings showing an embodiment in which a through groove 52 is provided perpendicular to the lengthwise direction of a slot 51 of a bracket body 50. In this embodiment, the through groove 52 passes through the bracket body 50 at a location slightly above the bottom surface of the slot 51. This through groove 52 is also provided so as to extend across a slider portion 53. This through groove 52 is used to allow passage of a wire and the like for adding a ligation function to an orthodontic bracket.

Figure 35:
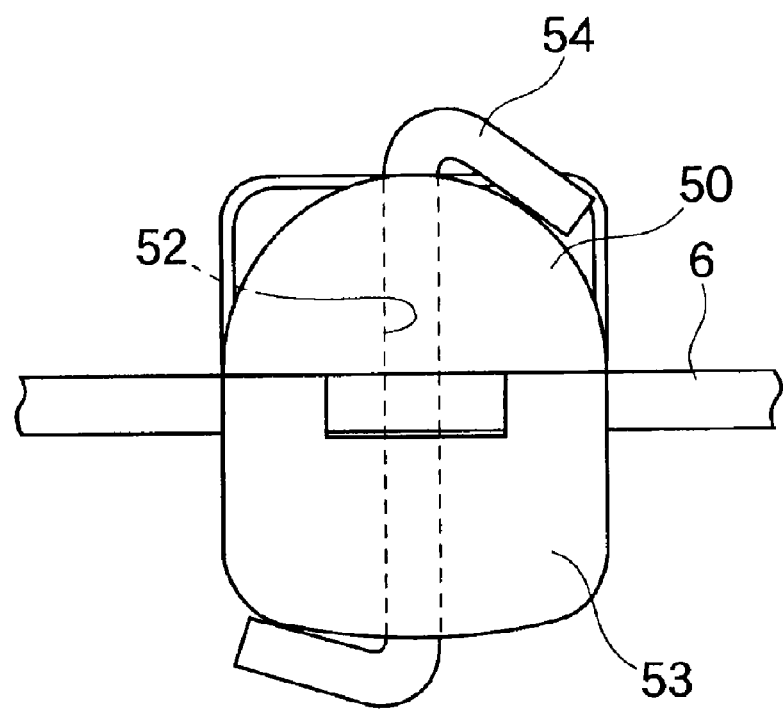
FIG. 35 is a plan view of the orthodontic bracket showing a configuration in which a wire passing through a through hole is attached and held with both ends bent in the fifth embodiment.
Figure 36:
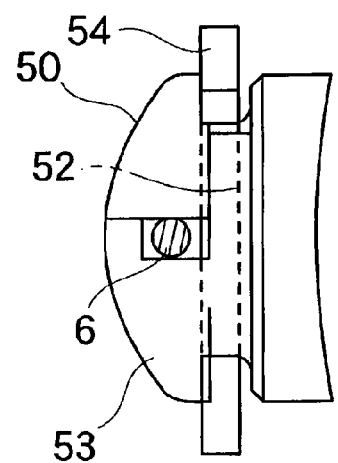
FIG. 36 is a front view of FIG. 35.

In the case of using for wire control as shown in FIGS. 35 and 36, for example, a wire 54 that matches the through hole 52 is caused to pass there through and the wire 54 is bent at both ends respectively, namely at the end on the side of the bracket body 50 and at the end on the side of the slider portion 53, to prevent it from coming out, thereby reducing the gap with respect to the archwire 6 in the center of the through groove 52 and enhancing elastic action of a thin wire in particular.

Figure 37:
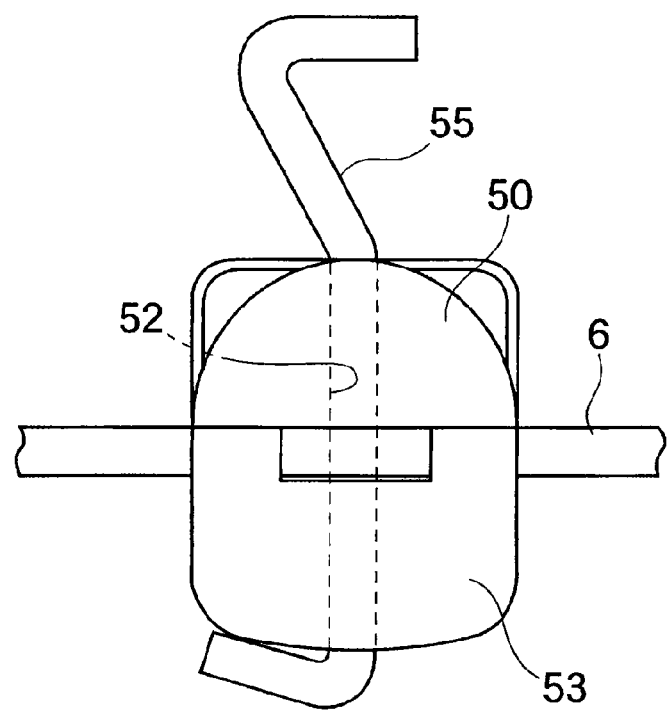
FIG. 37 is a plan view of the orthodontic bracket showing a configuration in which a square wire passing through a through hole is fastened and held with one end bent into the shape of a hook in the fifth embodiment.
Figure 38:
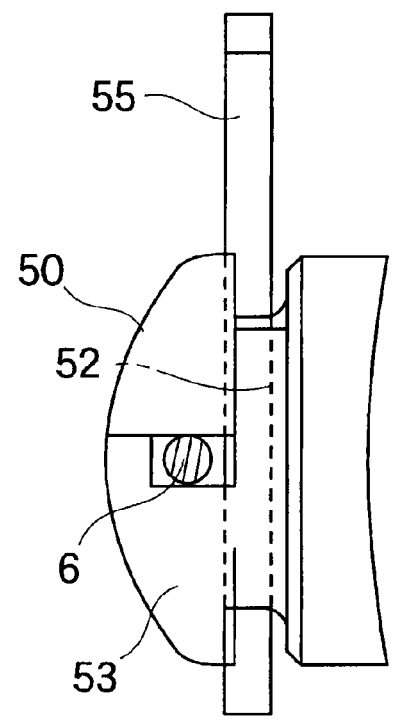
FIG. 38 is a front view of FIG. 37.

In contrast to wire control by adding thickness to both sides indicated by A and B of the through groove of the slider portion 22 explained previously with reference to FIG. 22, the action of the archwire 6 differs in the case of this embodiment, since the wire 54 is controlled by reducing the gap in the center of the through groove 52 without changing the cross-sectional shape of the slot. In addition, in the case of utilizing for attachment using a hook, a square wire 55 that matches the through groove 52 can be attached by causing it to pass there through and bending it to be in an arbitrary shape of a hook as shown in FIGS. 37 and 38. Therapeutic effect can be enhanced since the square wire 55 can be formed to be in the shape of a hook suitable for tooth movement.

Figure 39:
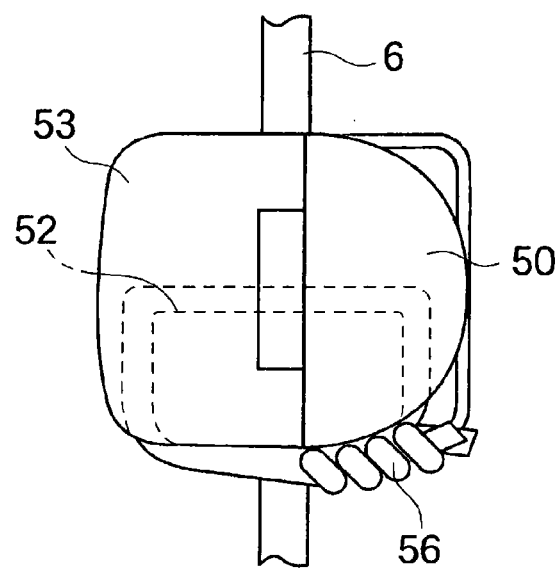
FIG. 39 is a plan view of the orthodontic bracket showing a configuration in which a ligature wire passing through a through groove is fastened and held in the fifth embodiment.
Figure 40:
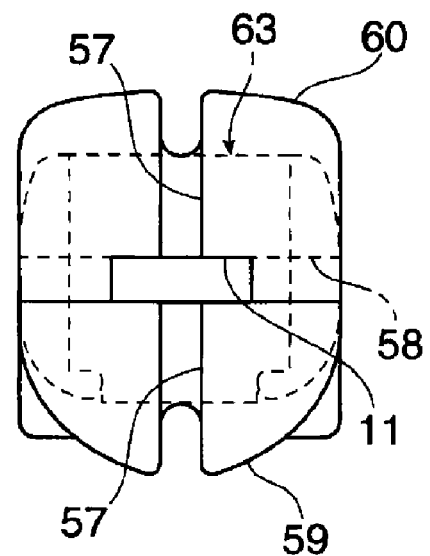
FIG. 40 is a plan view of an orthodontic bracket according to a sixth embodiment of the present invention showing a configuration in which a through groove is provided in the surface of a bracket body and slider portion.

In the case of application to ligation using a ligature wire, as shown in FIG. 39, unilateral ligation can be carried out by causing a ligature wire 56 to pass through the through groove 52 and fastening by hooking on the portion of the archwire 6 protruding to the outside. Since an orthodontic bracket as explained above can be attached to and detached from a bracket at a required location when necessary in the state of being attached to a tooth, it is advantageous in terms of aesthetic appearance, cleanability, operability and the like in the case of adding these functions.

Sixth Embodiment

In the following, explanation of a sixth embodiment will be made in accordance with FIGS. 40 to 45. This is an example of a configuration in which a through groove 57 is provided on the surface of the bracket body 1 and the slider portion 2 in a direction perpendicular to the lengthwise direction of the slot. In the case of the fifth embodiment, the through groove 52 was provided in a direction perpendicular to the lengthwise direction of a slot and this through groove 52 was made to pass through at a location slightly higher than the bottom surface of the slot. In contrast, in the configuration by this embodiment, the through groove 57 is provided so as to extend over wings in the surface of a bracket body 59 and a slider portion 60 in a direction perpendicular to the lengthwise direction of a slot 58 roughly in the center thereof.

Figure 41:
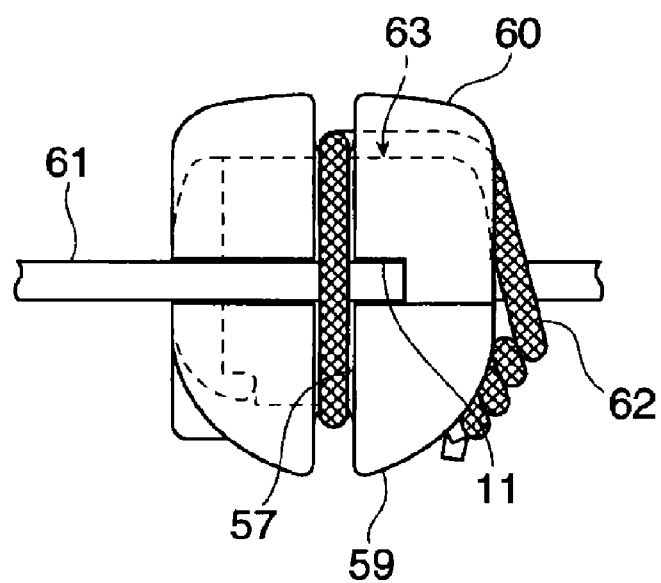
FIG. 41 is a plan view of the orthodontic bracket showing a configuration in which a ligature wire passing through a through groove is attached and held in the sixth embodiment.
Figure 42:
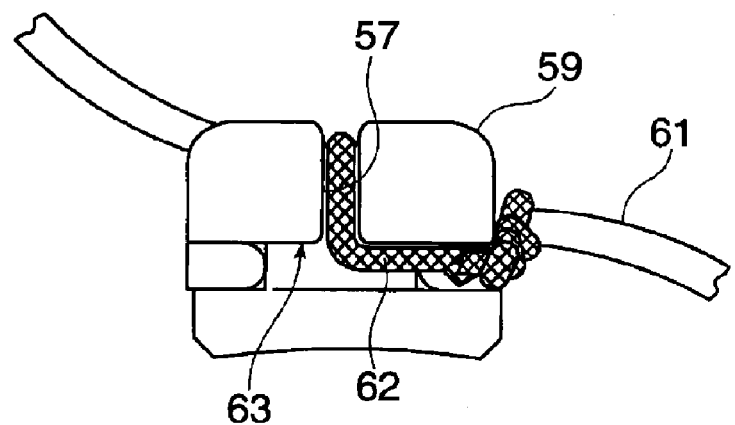
FIG. 42 is a front view of FIG. 41.
Figure 43:
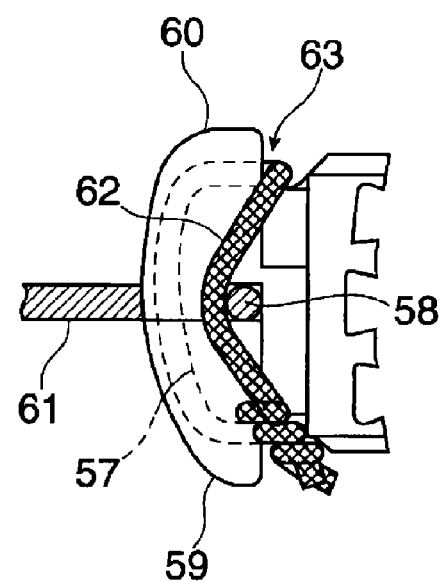
FIG. 43 is a side view of FIG. 41.

This configuration is effective for fixing a archwire 61, in the case of having the archwire attached with its one end protruding to the outside of the slot 58 as shown in the plan view of FIG. 41, the front view of FIG. 42 and the side view of FIG. 43. Namely, in this fixing method, a ligature wire 62 is first installed in the through groove 57 and hooked on the upper portion of the archwire 61. Then, the ligature wire 62 is wrapped around a wing 63, caused to pass through the overhang of the bracket body 59 and the slider portion 60 and brought to the outside.

A portion of the ligature wire 62 that has passed through the overhang of the wing 63 is again caused to pass through onto the upper side of the archwire 61 protruding outwards and fixed in position by tying both ends of the ligature wire 62 together. As a result, the archwire 61 is fixed, although only on one side, through being clamped by the bracket body 59 and the slider portion 60 by means of pressing force at two locations in the upper portion. In this case, it is preferable that one end of the slider groove 11, at which the archwire 61 protrudes outwards, is open or formed with a part of inclined groove to facilitate installation of the archwire 61.

Figure 44:
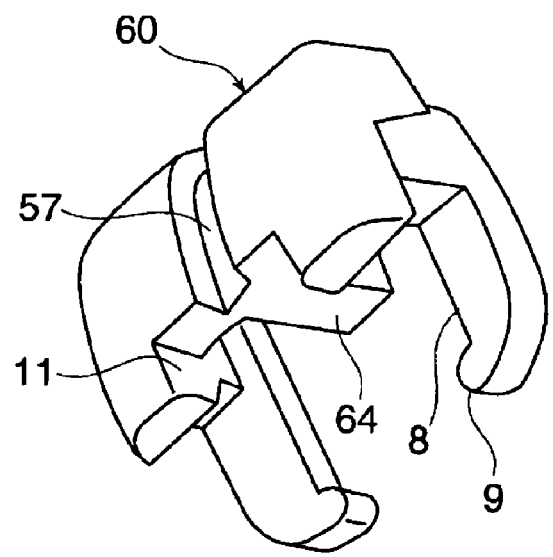
FIG. 44 is an external view of a slider portion alone in the sixth embodiment.
Figure 45:
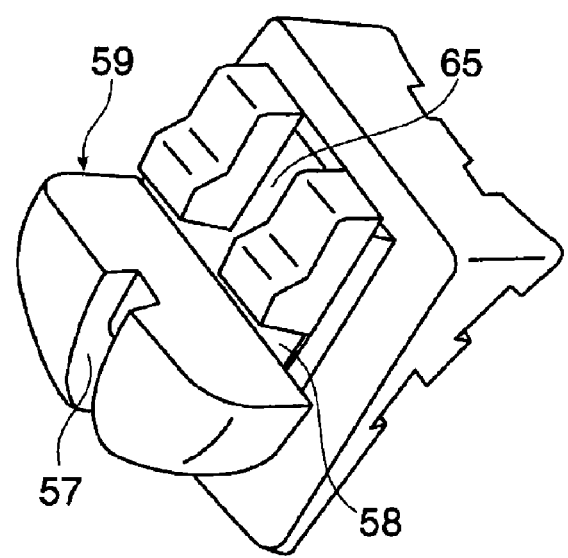
FIG. 45 is an external view of a bracket body alone in the sixth embodiment.

FIG. 44 is an external view showing the configuration of the slider portion 60 alone. In this configuration, the through groove 57 is provided in the surface in a direction perpendicular to the lengthwise direction of the slider groove 11. The bottom portion is increased in thickness to form a thick portion 64 in order retain the strength of the bottom portion even if the through groove 57 is provided. The configuration of the arms 8 and the sliding portions 9 is the same as that of the above-mentioned first embodiment. FIG. 45 is an external view showing the configuration of the bracket body 59 alone. Although the through groove 57 continuous with the slider portion 60 is also provided in the surface of this bracket body 59, an insertion groove 65, into which the thick portion 64 of the slider portion 60 is inserted through the slot 58, is provided in the lower portion of the installed portion of the slider portion 60. Since the bracket body 59 has adequate thickness in the vicinity of this insertion groove 65, there is no reduction in strength as a result of providing the insertion groove 65.

Seventh Embodiment

Figure 46:
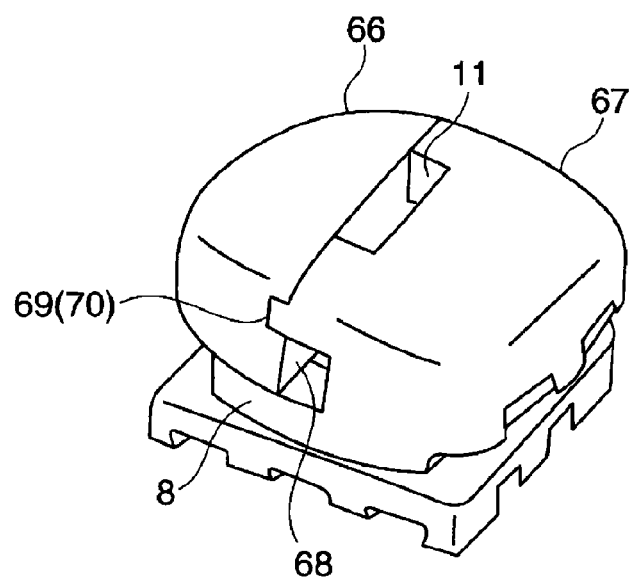
FIG. 46 is an external view of an orthodontic bracket according to a seventh embodiment of the present invention showing a configuration in which a slider portion is attached to a bracket body.
Figure 47:
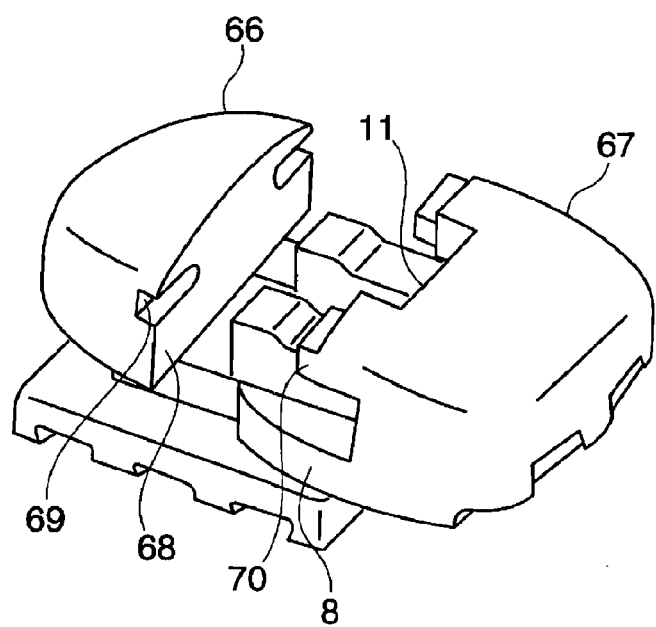
FIG. 47 is an external view of the orthodontic bracket according to the seventh embodiment showing a configuration in which a slider portion is extracted from a bracket body.

In the following, explanation of a seventh embodiment will be made in accordance with FIGS. 46 and 47. This seventh embodiment is composed so that strength is mutually reinforced when an archwire is inserted into a bracket body 66 followed by attaching a slider portion to be integrated into a single unit. FIG. 46 is an external view showing a configuration in which a slider portion 67 is attached to the bracket body 66, while FIG. 47 is an external view showing a state in which the slider portion 67 is detached from the bracket body 66. As shown in the drawings, recesses 69 are formed in the bracket body 66 on a lateral surface of the upper portion of a slot sidewall 68 where an archwire is installed.

On the other hand, projections 70, which can be inserted into the recesses 69, are provided at locations corresponding to the recesses 69 in the slider portion 67. This combination of recesses and projections is provided to be present at two locations in the lengthwise direction on both sides of the slider groove 11. When an archwire (not shown) is attached to a slot and the slider portion 67 is inserted into the bracket body 66, the projections 70 of the slider portion 67 are inserted into the recesses 69 of the bracket body 66 enabling both to form a single unit. As a result, while the archwire is held through being clamped in the slider portion 67 within a rectangle that is open on one side and closed on three sides, the slider portion 67 is simultaneously held through being clamped by the bracket body 66 with the projection 70 and the arms 8.

As a result of employing such a configuration, integration of the bracket body 66 and the slider portion 67 is strengthened and deformation such as rotation or the like accompanied by ligation of an archwire can be reduced. Although this configuration employing the combination of recess and projection has the projection 70 on the slider portion 67 side and the recess 69 on the bracket body 66 side, conversely a configuration may be employed in which a recess is provided on the slider portion 67 side and a projection is provided on the bracket body 66 side.

In this manner, the orthodontic bracket according to this embodiment is composed to be of a sliding type using a structure that has a rounded shape with few surface irregularities, hence irritation of mucosal membranes after installing on teeth of a patient is reduced, cleanability is improved as result of employing a structure that facilitates brushing of teeth and suppresses accumulation of residual food particles and management of oral hygiene becomes easier. Further, maintenance is improved for attaching and detaching archwires. Moreover, as a result of employing a configuration that is free of protruding wings or structural surface irregularities for use in a self-ligating method, which was present in the prior art, configuration with a satisfactory aesthetic appearance has been obtained. In addition, while a clasp produced through shaping a metal wire is frequently used to maintain, attach and remove retainers or tooth positioners, the shape of this orthodontic bracket with few surface irregularities may be used as a hook for maintenance, attachment and removal of a retainer or the like instead of the clasp.

Moreover, this configuration that is free of irregularities make the structure itself simple so that damage hardly occurs. In terms of function, a configuration with a slider as ligation means enables procedures such as replacing an archwire to be carried out rapidly and reliably without causing the slider to come off and, in the case of replacing the slider for archwire control or in the case of damage in the slider, accommodation can be made easily simply by replacing the slider alone, thereby facilitating management.

Eighth Embodiment

Figure 48:
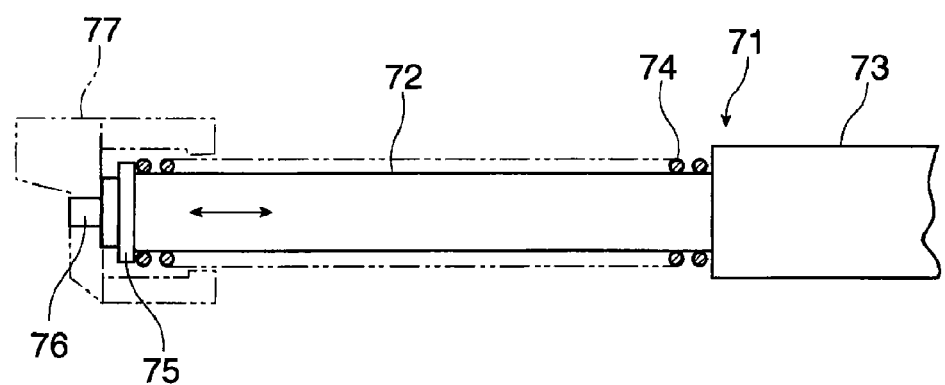
FIG. 48 is a front view of an operating tool.

In the following, explanation of an eighth embodiment will be made in accordance with FIG. 48. This embodiment relates to a slot opener. While the slot opener shown in FIG. 19 employs a configuration in which the projection 15 is fixedly provided on the body, the projection is able to move in this embodiment. A support column 72 of a slot opener 71 is supported by a handle portion 73 to allow the slot opener 71 to be guided with forward and backward movement by prescribed dimensions. A coil spring 74 is interposed on the support column 72 and the coil spring 74 pushes a step portion 75 provided on the end of the support column 72 and urges the support column 72 outwards.

The end of the support column 72 has a projection 76 equivalent to the above-mentioned projection 15. In addition, a guiding member 77 that matches the shape of the bracket is provided around the vicinity of the projection 76. This guiding member 77 is composed so as to be replaced according to the shape of the bracket. The slot opener 71 composed in this manner is operated in the same manner as the previously described slot opener 14 by inserting the projection 76 into the slider groove 11 and extracting a slider portion from a bracket body. At this time, since the projection 76 is pushed with the urging force of the coil spring 74 and the guiding member 77 is positioned by fitting into the bracket, the slot opener 71 can be operated accurately and smoothly without applying excessive force to the bracket.

Procedures performed by orthodontists are typically complex due to the small size of the slider groove 11. However, use the slot opener 71 as an operating tool enables the projection 76 to accurately fit into the slider groove 11 in an operation with few occurrence of trouble by aligning the guiding member 77 with the bracket and rotating the guiding member 77 as viewing it. The slider portion can be easily extracted in the same manner as previously described by rotating the projection 76 by 90 degrees. Although embodiments of the present invention have been explained, it goes without saying that the present invention is not limited to these embodiments.

What is claimed is:

1. An orthodontic bracket for orthodontic treatment, which has a face for joining to a tooth surface in the a lower portion thereof and has a groove for holding an archwire provided in a center thereof so as to slide freely and/or be fixed, the bracket comprising:

a bracket body that includes the groove for holding the archwire; and a slider portion guided by the bracket body, the slider portion holds the archwire so as to be guided by three surfaces of a through groove consisting of an upper portion, side portion, and lower portion of the slider portion while being able to move relative to the bracket body, wherein a first through groove is provided in a first overhang portion of an outer sidewall of the bracket body, wherein the first overhang portion extends along the direction of installation of the archwire, a second through groove is provided in a second overhang portion of an outer sidewall of the slider portion, wherein the second overhang portion extends along the direction of installation of the archwire, the slider portion has a surface area that is approximately half of the surface area of the bracket body when viewed from above, the slider portion is configured to be attached to and detached from the bracket body while moving forward and backward relative to the bracket body along a straight line by means of two guide portions provided on the bracket body and positioned at the lower portion of the archwire, the slider portion has two elastically deformable holding portions for fixing and holding the archwire using the elasticity of the slider portion itself at the position of the two guide portions of the bracket body, and the two elastically deformable holding portions pinch the two guide portions of the bracket body.

2. The orthodontic bracket according to claim 1, wherein the slider portion has a concave slider groove for detachment for attaching and detaching the archwire through enabling the slider portion to move for detachment with respect to the bracket body.

3. The orthodontic bracket according to claim 1, wherein the bracket body and the slider portion are provided, in the lower portion of a groove for locking the archwire, with a through groove which extends over both of the bracket body and the slider portion in a direction that transverses the groove for locking the archwire.

4. The orthodontic bracket according to claim 1, wherein the bracket body and the slider portion are provided, in a surface of the upper portion of the groove for locking the archwire, with a through groove which extends over both of the bracket body and the slider portion in a direction that transverses the groove for locking the archwire.

5. The orthodontic bracket according to claim 1, wherein the bracket body and the slider portion are provided with recesses and projections mutually engageable and disengageable at contact sites on an upper portion of the archwire locking sidewall.

6. The orthodontic bracket according to claim 2, wherein the concave slider groove for detachment includes a cutout portion, of which one side is open and which has a rectangular cross-section, at the upper position of the archwire to be attached and detached.

7. The orthodontic bracket according to claim 3, wherein the slider portion is provided with a protruding thick portion at a lower portion of the through groove and the bracket body is provided with a recess into which the thick portion is inserted.

8. The orthodontic bracket according to claim 6, wherein the concave slider groove for detachment has a shape in which one end at a position of the upper portion is open in a lengthwise direction of the archwire.

9. The orthodontic bracket according to claim 6, wherein the concave slider groove for detachment is a groove having a shape into which is inserted an operating tool having an inserting portion that is urged with the elastic force by an elastic body.

10. The orthodontic bracket according to claim 4, wherein the slider portion is provided with a protruding thick portion at the lower portion of the through groove and the bracket body is provided with a recess into which the thick portion is inserted.

* * * * *